(12) United States Patent
Williams, Jr.

(10) Patent No.: US 7,371,522 B2
(45) Date of Patent: May 13, 2008

(54) USE OF POLYMORPHISM OF THE SEROTONIN TRANSPORTER GENE PROMOTER AS A PREDICTOR OF DISEASE RISK

(75) Inventor: Redford B. Williams, Jr., Hillsborough, NC (US)

(73) Assignee: Duke University, Durham, NC (US)

( * ) Notice: Subject to any disclaimer, the term of this patent is extended or adjusted under 35 U.S.C. 154(b) by 278 days.

(21) Appl. No.: 10/625,134

(22) Filed: Jul. 23, 2003

(65) Prior Publication Data

US 2004/0126786 A1    Jul. 1, 2004

Related U.S. Application Data

(63) Continuation of application No. 09/698,870, filed on Oct. 27, 2000, now abandoned.

(60) Provisional application No. 60/162,390, filed on Oct. 29, 1999.

(51) Int. Cl.
*C12Q 1/68* (2006.01)
*C12P 19/34* (2006.01)

(52) U.S. Cl. .................. 435/6; 435/91.1; 435/91.2

(58) Field of Classification Search .............. None
See application file for complete search history.

(56) References Cited

U.S. PATENT DOCUMENTS 5,418,162 A     5/1995  Blakely et al.
6,653,073 B1 *  11/2003 Comings et al. ............ 435/6

FOREIGN PATENT DOCUMENTS

WO     WO 99/42619    *  8/1999  ............... 435/6

OTHER PUBLICATIONS

Persico et al; American Journal of Medical Genetics, vol. 96, pp. 123-127, 2000.*
Kunugi et al; American Journal of Medical Genetics, vol. 96, pp. 307-309, 2000.*
Arinami et al; Thrombosis Haemostasis, vol. 81, pp. 853-856, Jun. 1999.*
Grassi et al; Circulation, vol. 90, pp. 248-253, 1994.*
Kendler et al; Arch. Gen. Psychiatry, vol. 62, May 2005, pp. 529-535.*
Williams et al; Neuropsychopharmacology, 2003, vol. 28, pp. 533-541.*
Yeo et al; Gut, 2004, vol. 53, pp. 1452-1458.*
Wurtman, R.J. Metabolism Clinical and Experimental, vol. 54, pp. 16-19, 2005.*
Rozanski et al; Circulation, vol. 99, pp. 2192-2217; 1999, see abstract.*

(Continued)

*Primary Examiner*—Jehanne S Sitton
(74) *Attorney, Agent, or Firm*—Myers Bigel Sibley & Sajovec, P.A.

(57) ABSTRACT

The present invention provides a method of screening subjects for disease risk. The method comprises determining the serotonin transporter gene promoter genotype of a subject. The serotonin transporter gene promoter genotype is used to indicate whether or not the subject is at increased risk of disease. The method is particularly adapted to screening for risk of disease in response to stress, and accordingly can be used to indicate interventions that manage stress, and hence reduce disease risk, in susceptible or higher-risk individuals.

5 Claims, 17 Drawing Sheets

5HTTLPR Genotypes and Mean Arterial Pressure Response to Stress

OTHER PUBLICATIONS

Hanna et al; Neuropsychopharmacology, vol. 18, Feb. 1998, pp. 102-111.*

Gabe et al; Molecular Psychiatry vol. 10:220-224; 2005.*

Arinami, Tadao, et al., A Synergistic Effect of Serotonin Transporter Gene Polymorphism and Smoking in Association with CHD, *Thromb. Haemost.*, vol. 81, No. 6, pp. 853-856 (Jun. 1999).

Rozanski et al. "Impact of Psychological Factors on the Pathogenesis of Cardiovascular Disease and Implications for Therapy" *Circulation* 99:2192-2217 (1999).

Kamarck et al. "Exaggerated Blood Pressure Responses During Mental Stress Are Associated With Enhanced Carotid Atherosclerosis in Middle-Aged Finnish Men" *Circulation* 96:3842-3848 (1997).

Matthews et al. "Stress-Induced Pulse Pressure Change Predicts Women's Carotid Atherosclerosis" *Stroke* 29:1525-1530 (1998).

Everson et al. "Stress-Induced Blood Pressure Reactivity and Incident Stroke in Middle-Aged Men" *Stroke* 32:1263-1270 (2001).

Everson et al. "Anger Expression and Incident Stroke: Prospective Evidence From the Kuopio Ischemic Heart Disease Study" *Stroke* 30:523-528 (1999).

Coto et al. "5-Hydroxytryptamine $5HT_{2A}$ receptor and 5-hydroxytryptamine transporter polymorphisms in acute myocardial infarction" *Clinical Science* 104:241-245 (2003).

Fumeron et al. "Serotonin Transporter Gene Polymorphism and Myocardial Infarction" *Circulation* 105:2943-2945 (2002).

Higley et al. "Low Central Nervous System Serotonergic Activity Is Traitlike and Correlates with Impulsive Behavior" *Annals New York Academy of Sciences* 836-36-56 (1997).

Lesch et al. "Association of Anxiety-Related Traits with a Polymorphism in the Serotonin Transporter Gene Regulatory Region" *Science* 274:1527-1531 (1996).

Lynch et al. "Does Low Socioeconomic Status Potentiate The Effects of Heightened Cardiovascular Responses to Stress on the Progression of Carotid Atherosclerosis?" *American Journal of Public Health* 88(3):389-394 (1998).

Nordin et al. "Acid Monoamine Metabolites in the CSF of Healthy Controls Punctured Without Preceding Strict Bedrest: A Retrospective Study" *J. Psychiat. Res.* 30(2):127-133 (1996).

Roy et al. "Acting Out Hostility in Normal Volunteers: Negative Correlation With Levels of 5HIAA in Cerebrospinal Fluid" *Psychiatry Research* 24:187-194 (1988).

Smeraldi et al. "Polymorphism within the promoter of the serotonin transporter gene and antidepressant efficacy of fluvoxamine" *Molecular Psychiatry* 3(6):508-511 (1998).

Williams et al. "Central Nervous System Serotonin Function and Cardiovascular Responses to Stress" *Psychosomatic Medicine* 63:300-305 (2001).

* cited by examiner

Fig. 1--Serotonin Transporter Promoter Genotypes and CSF 5HIAA
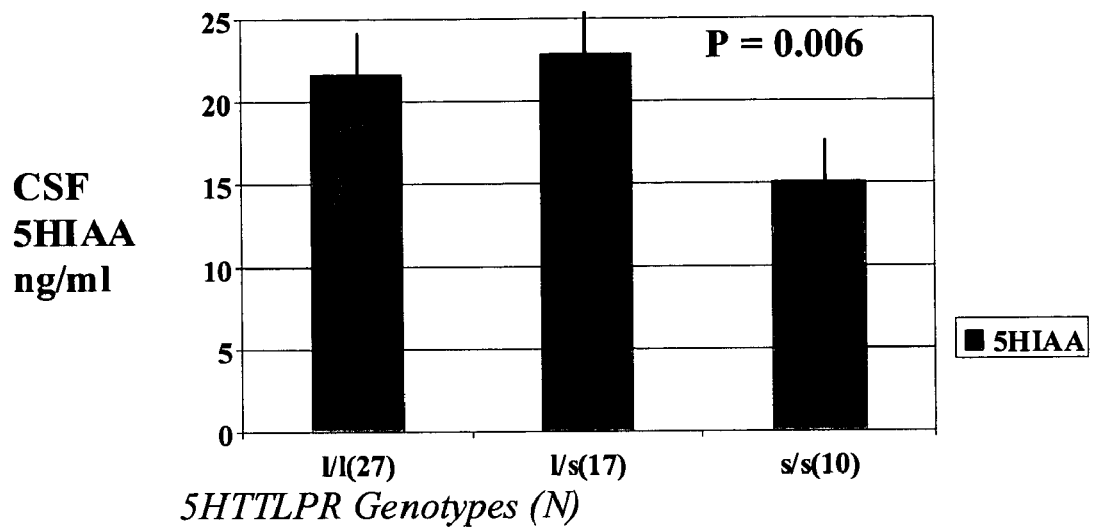
Fig. 2 5HTTLPR Genotypes & Hamilton Depression Rating Scale Scores After Fluvoxamine Rx
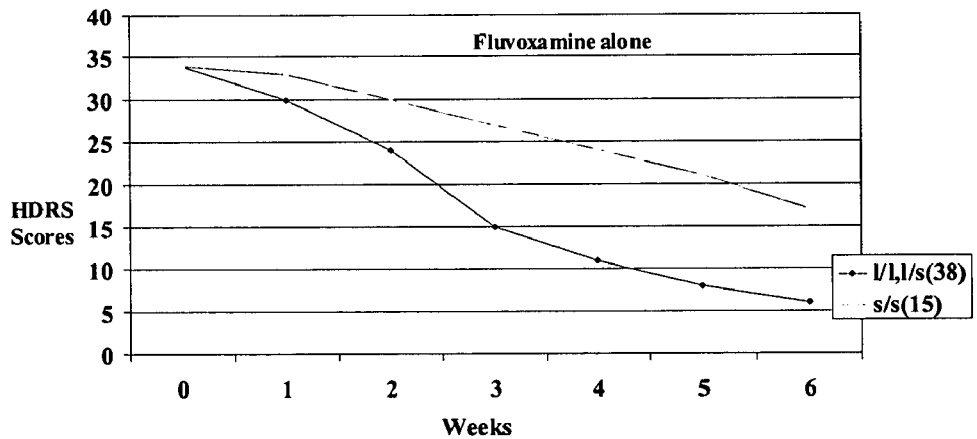
*Source: Molecular Psychiatry 1998;3:508-11)*

Fig. 3 5HTTLPR Genotypes & Hamilton Depression Rating Scale Scores After Fluvoxamine Rx Plus Pindolol
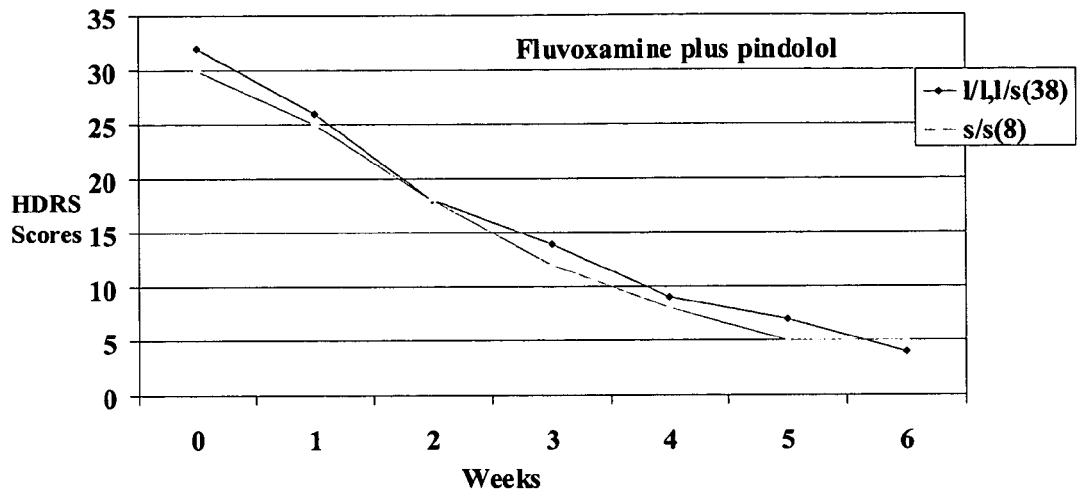
*Source: Molecular Psychiatry 1998;3:508-11)*
Fig 4. 5HTTLPR Genotypes and Mean Arterial Pressure Response to Stress
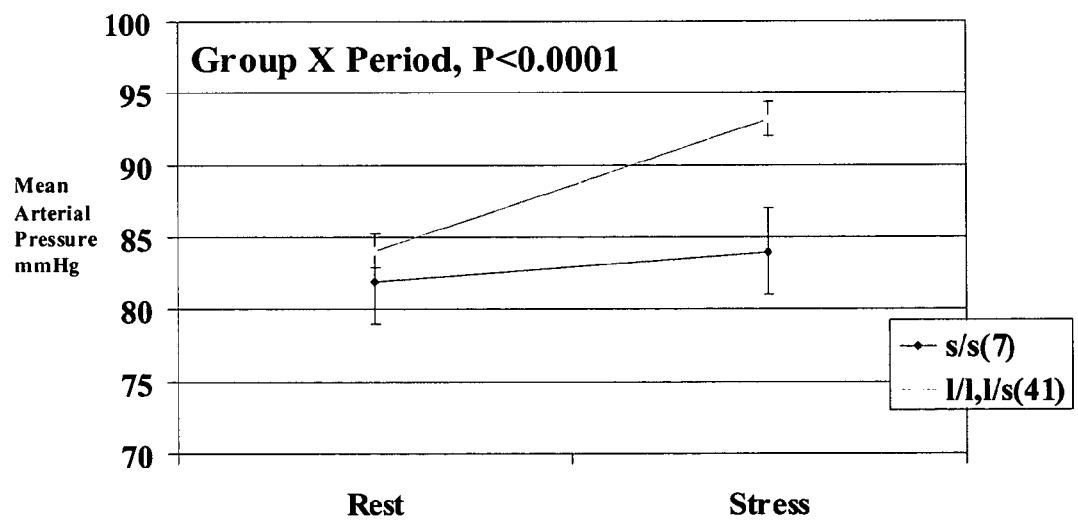

Fig. 5. CSF 5HIAA Levels and Mean Arterial Pressure Responses to Stress
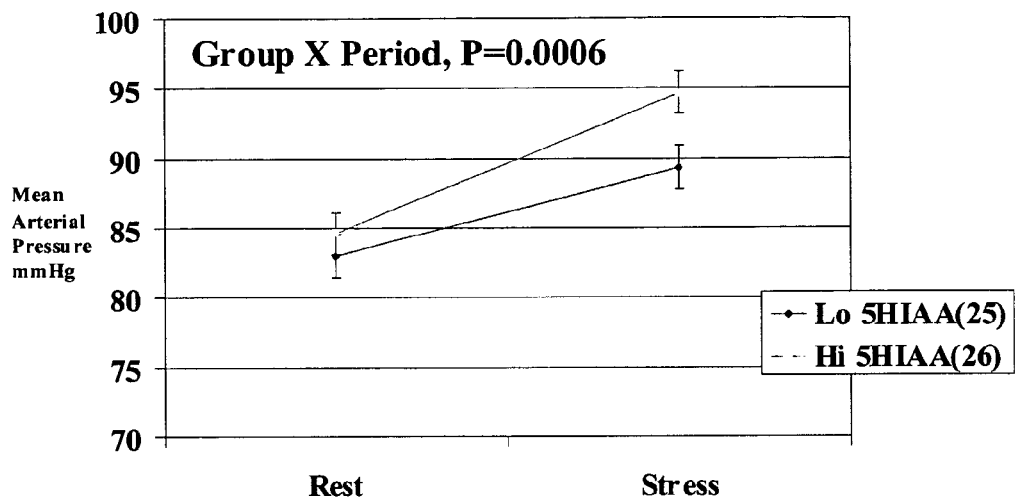
Fig. 6. 5HTTLPR Genotypes and Heart Rate Responses to Stress
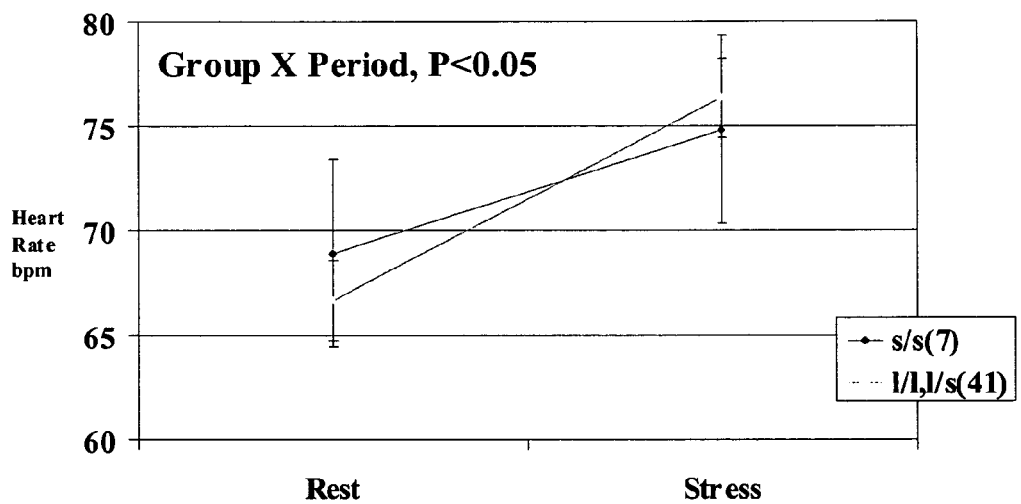

Fig. 7. CSF 5HIAA Levels and Heart Rate Responses to Stress
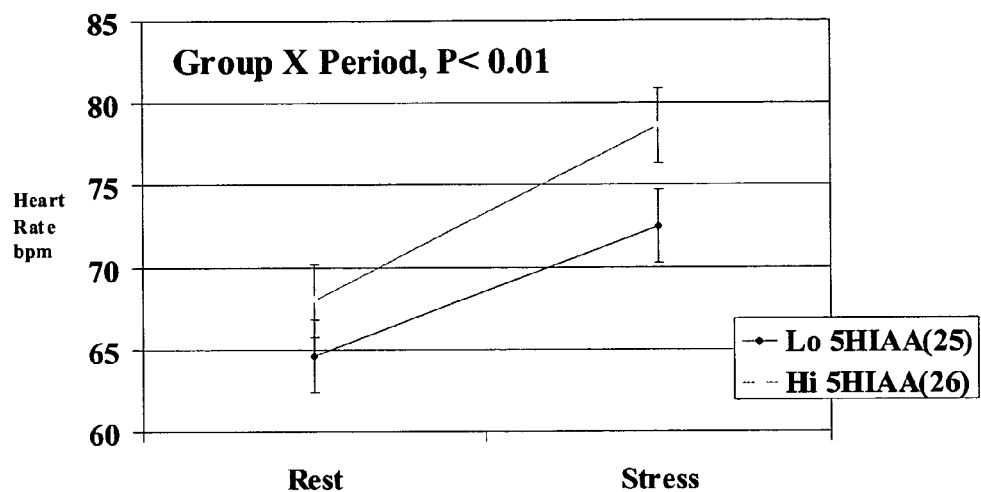
Fig. 8. 5HTTLPR Genotypes and Epinephrine Levels On Sham Tryptophan Depletion Day
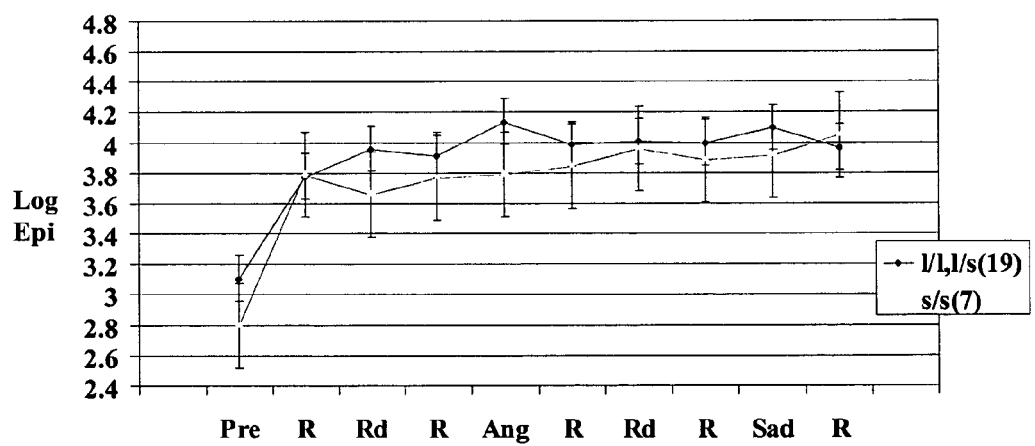

Fig. 9. 5HTTLPR Genotypes and Epinephrine Levels On Active Tryptophan Depletion Day
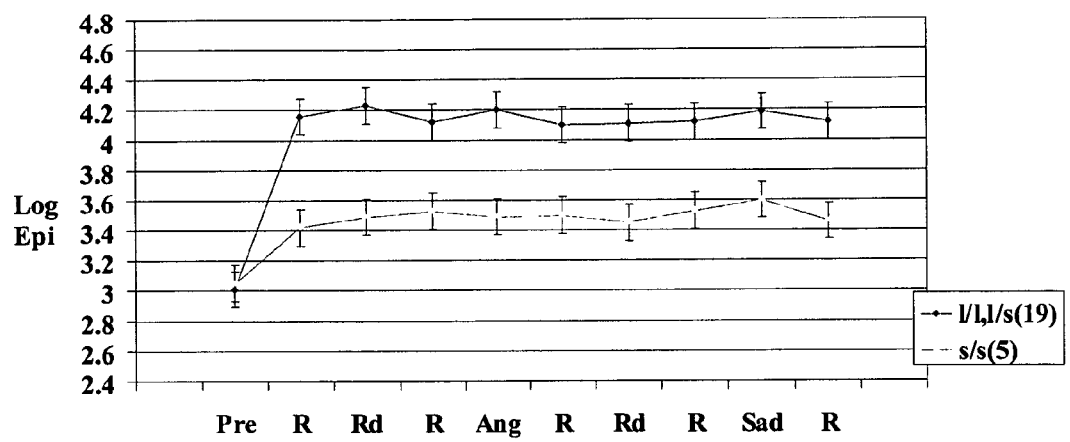
Fig. 10. 5HTTLPR Genotypes and Norepinephrine Levels On Sham Tryptophan Depletion Day
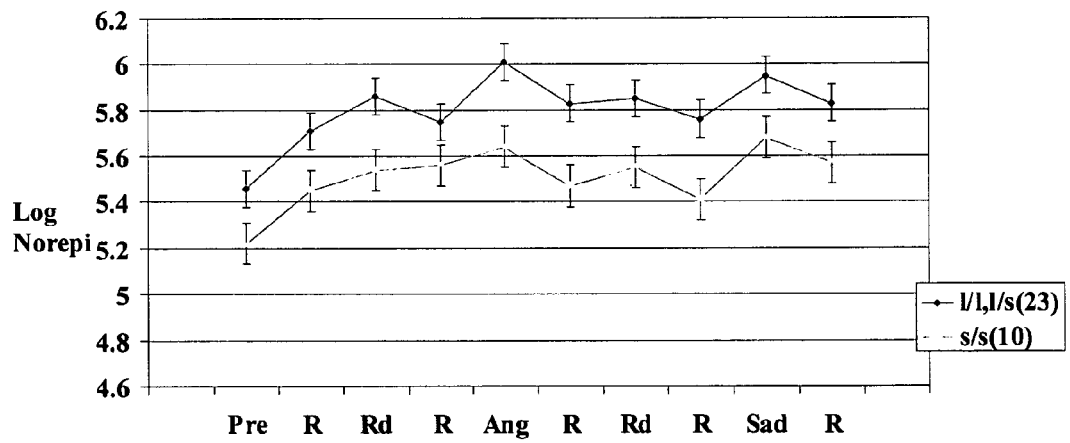

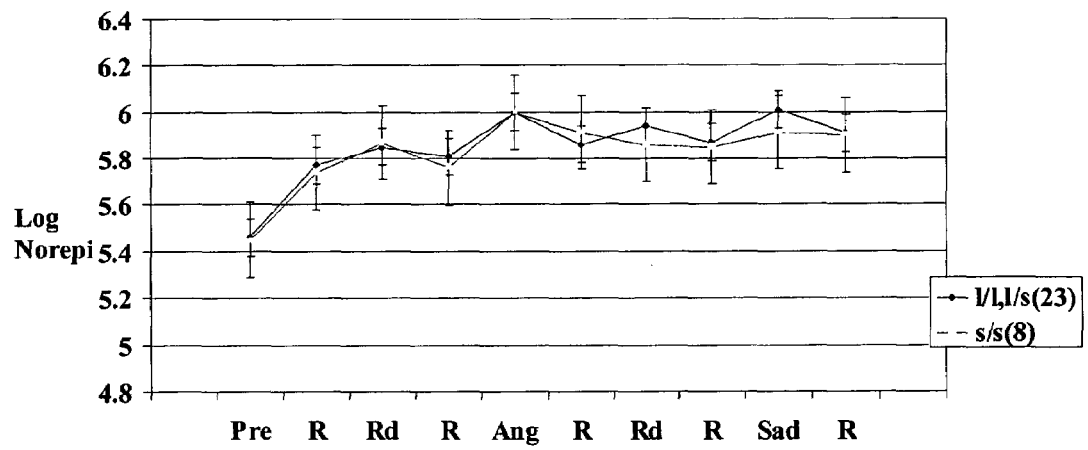
Fig. 11. 5HTTLPR Genotypes and Norepinephrine Levels On Active Tryptophan Depletion Day
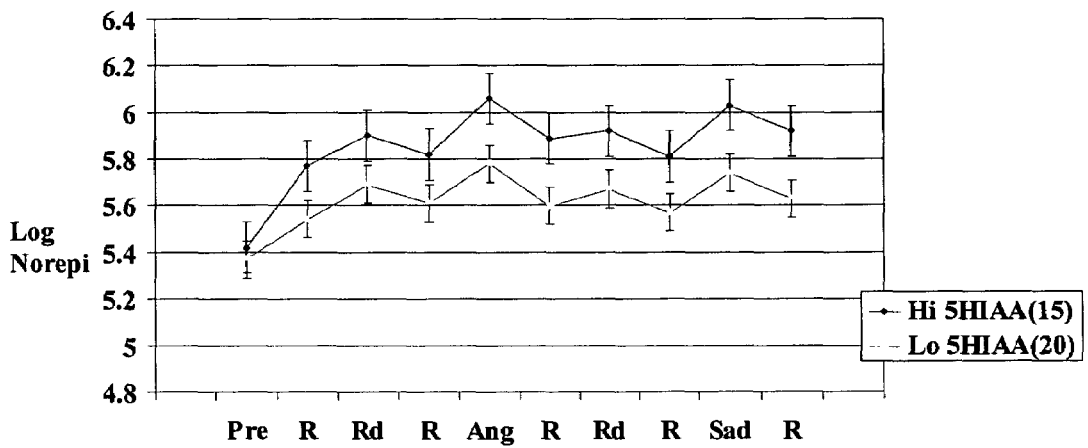
Fig. 12. CSF 5HIAA Levels and Norepinephrine Levels On Sham Tryptophan Depletion Day Fig. 13. CSF 5HIAA Levels and Norepinephrine Levels On Active Tryptophan Depletion Day
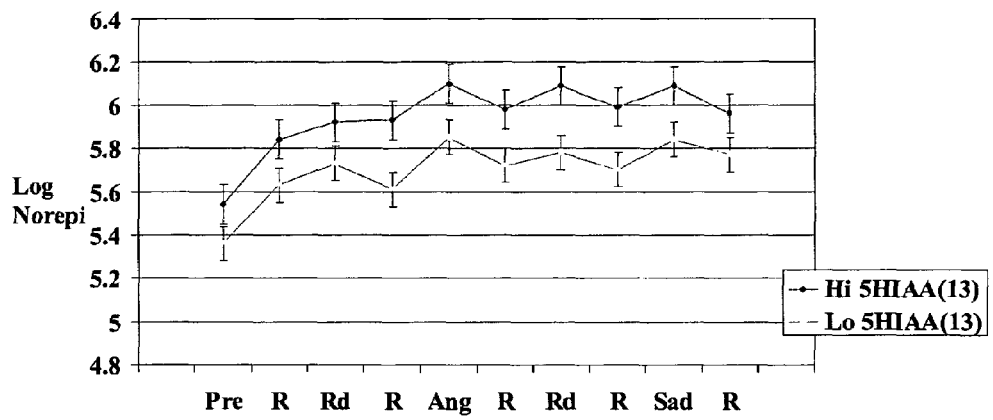
Fig. 14. CSF 5HIAA Levels and Norepinephrine Levels On Sham Tryptophan Infusion Day
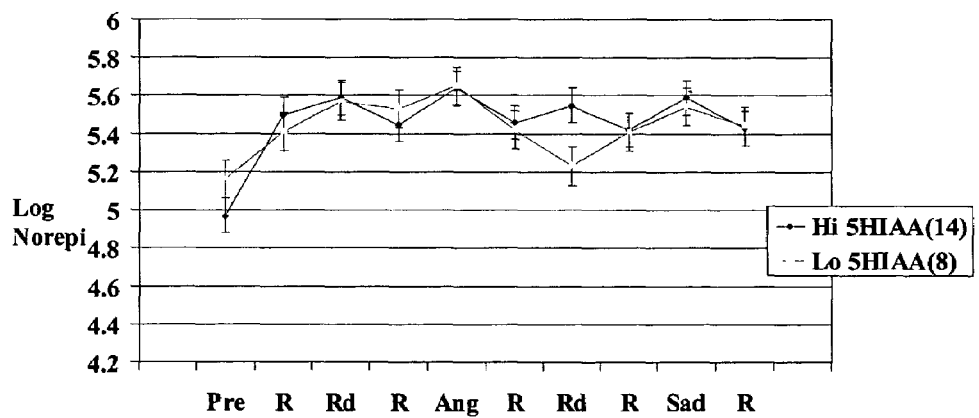

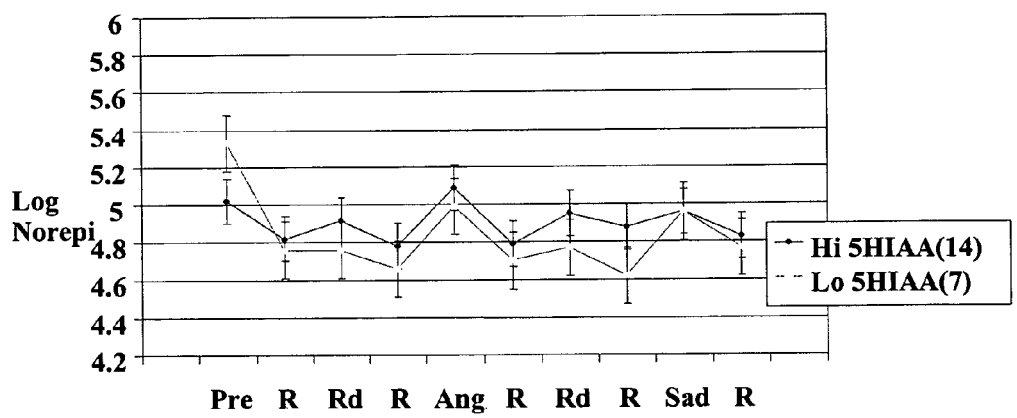
Fig. 15. CSF 5HIAA Levels and Norepinephrine Levels On Active Tryptophan Infusion Day
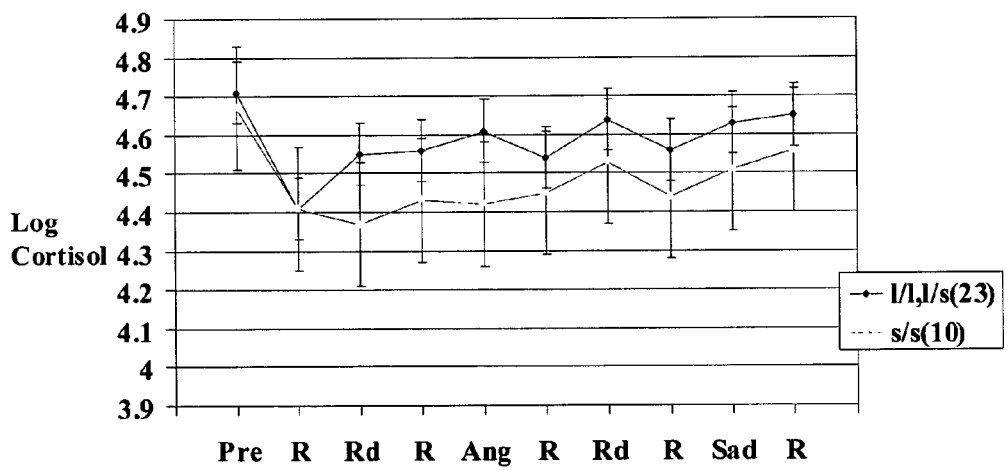
Fig. 16. 5HTTLPR Genotypes and Cortisol Levels On Sham Tryptophan Depletion Day Fig. 17. 5HTTLPR Genotypes and Cortisol Levels On Active Tryptophan Depletion Day
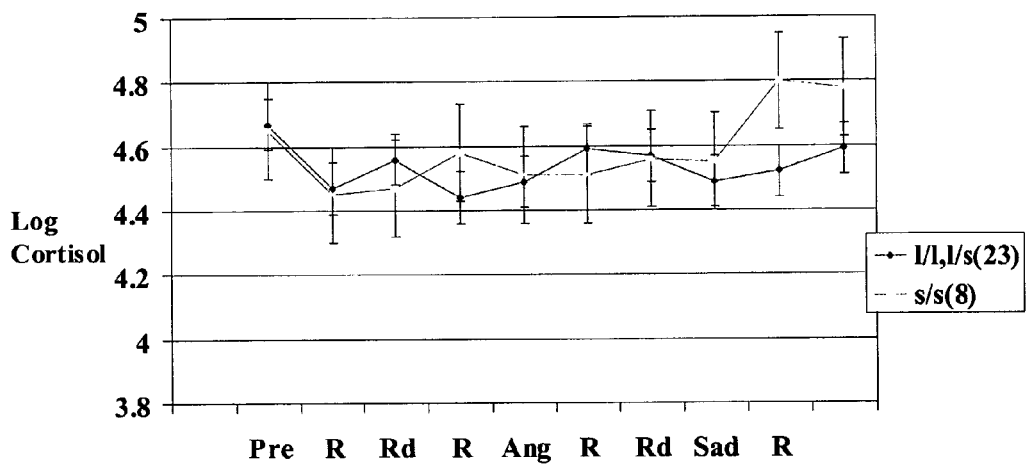
Fig. 18. CSF 5HIAA Level and Cortisol Levels on Sham Tryptophan Depletion Day
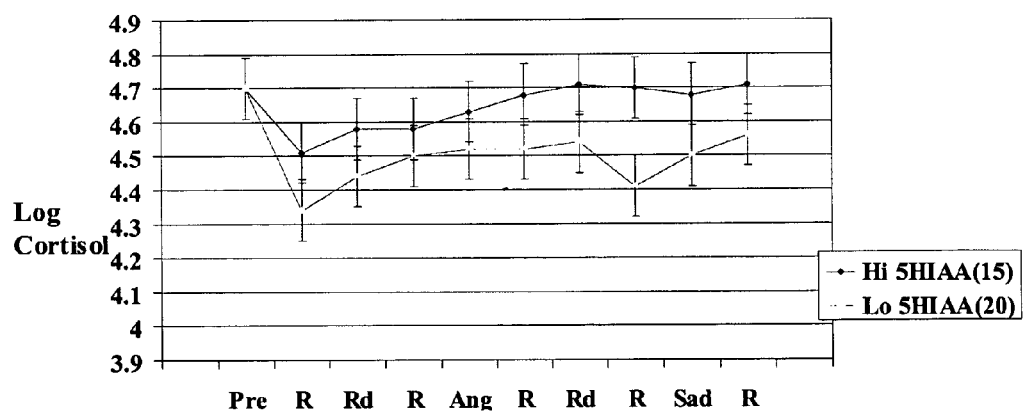

Fig. 19. CSF 5HIAA Level and Cortisol Levels on Active Tryptophan Depletion Day
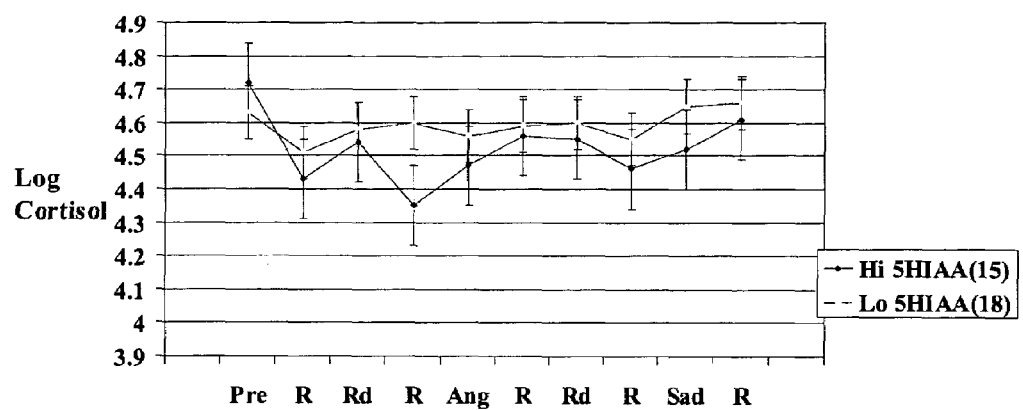
Fig. 20. CSF 5HIAA Level and Cortisol Levels on Sham Tryptophan Infusion Day
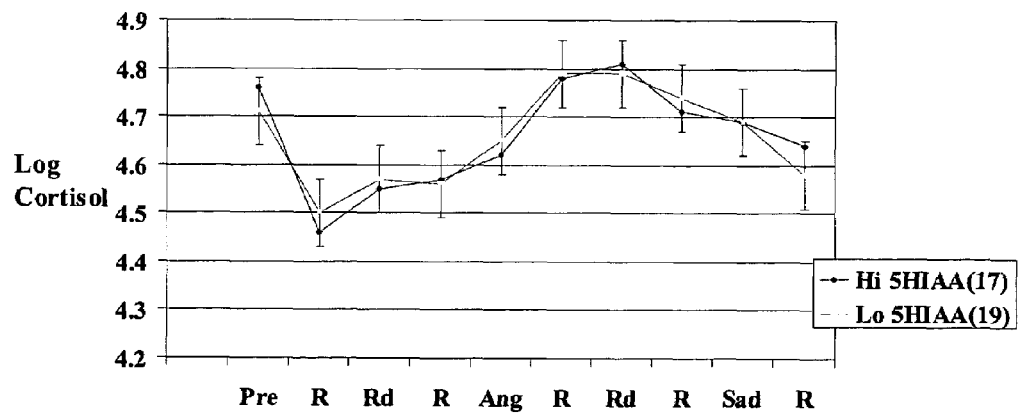

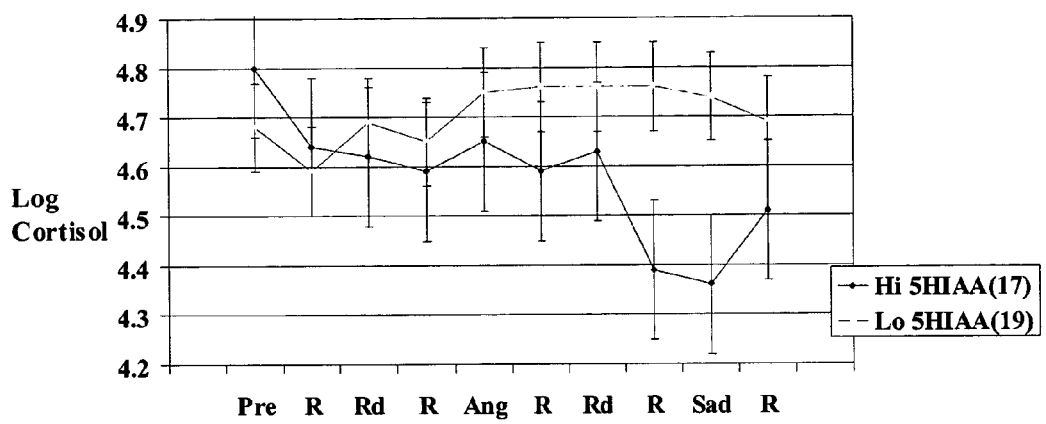
Fig. 21. CSF 5HIAA Level and Cortisol Levels on Active Tryptophan Infusion Day
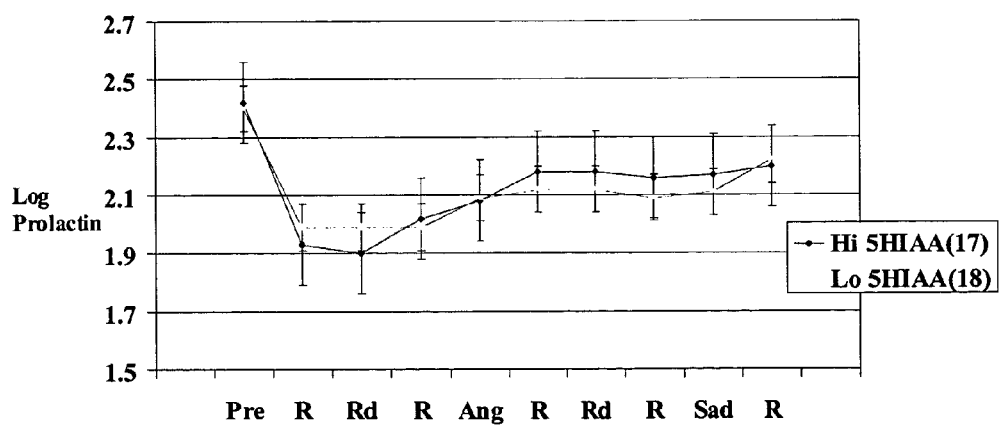
Fig. 22. CSF 5HIAA Levels and Prolactin Levels On Sham Tryptophan Infusion Day Fig. 23. CSF 5HIAA Levels and Prolactin Levels On Active Tryptophan Infusion Day
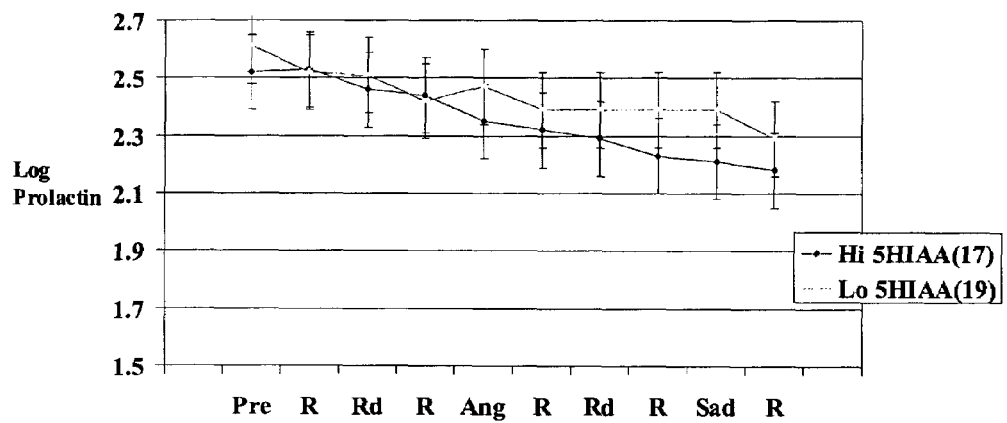
Fig. 24. CSF 5HIAA Levels and Prolactin Levels On Sham Tryptophan Depletion Day
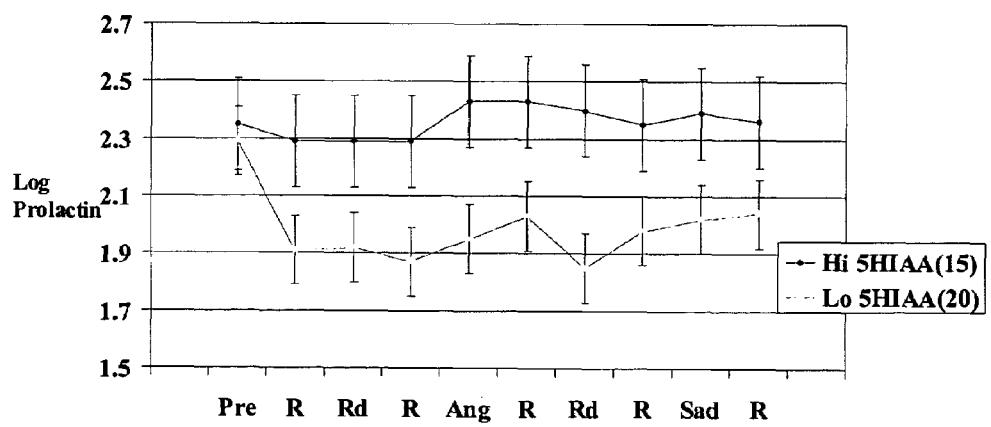

Fig. 25. CSF 5HIAA Levels and Prolactin Levels On Active Tryptophan Depletion Day
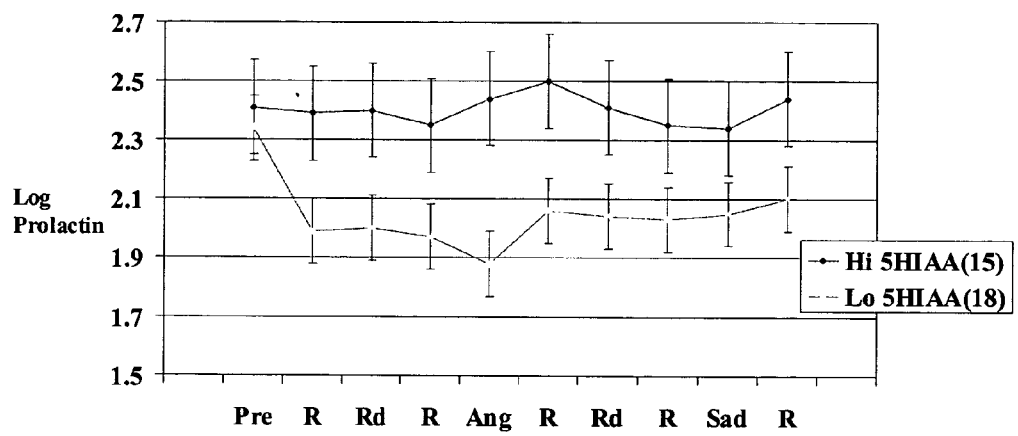
Fig. 26. 5HTTLPR Genotypes and Prolactin Levels On Sham Tryptophan Depletion Day
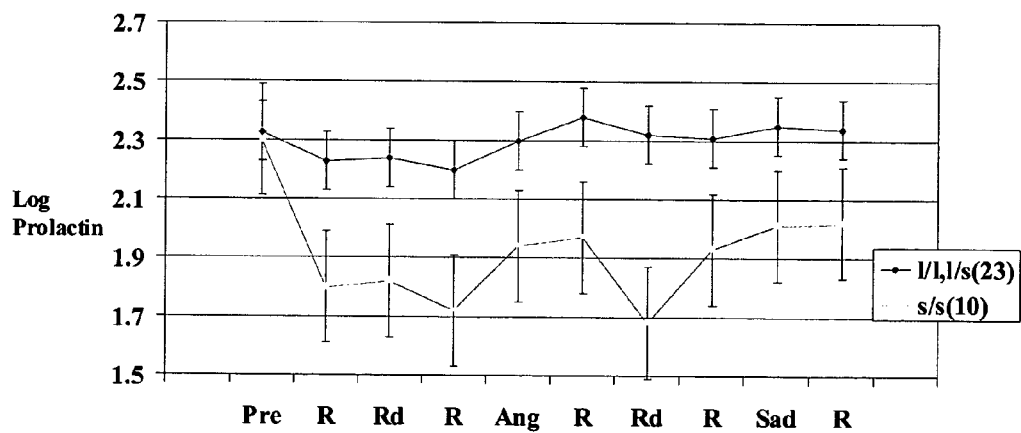

Fig. 27. 5HTTLPR Genotypes and Prolactin Levels On Active Tryptophan Depletion Day
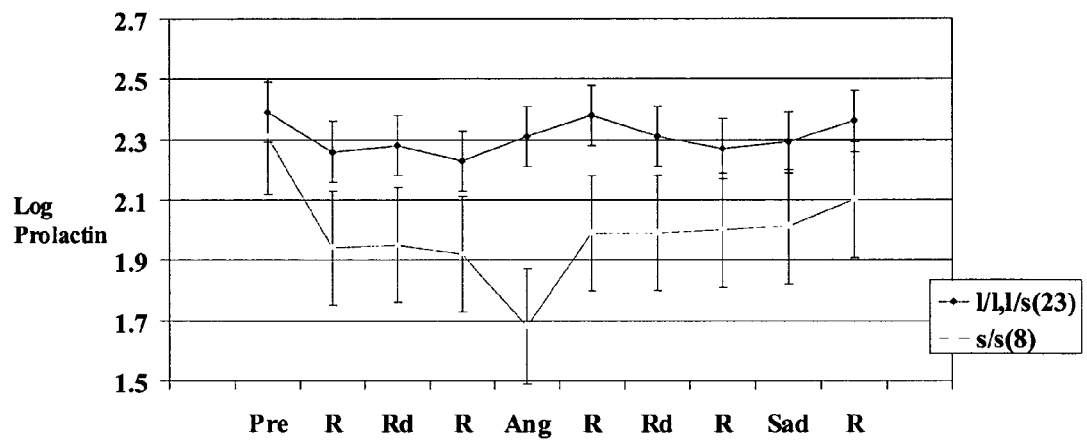
Fig. 28. CSF 5HIAA & CD-11a Response to Sham (Saline) Infusion & Stress
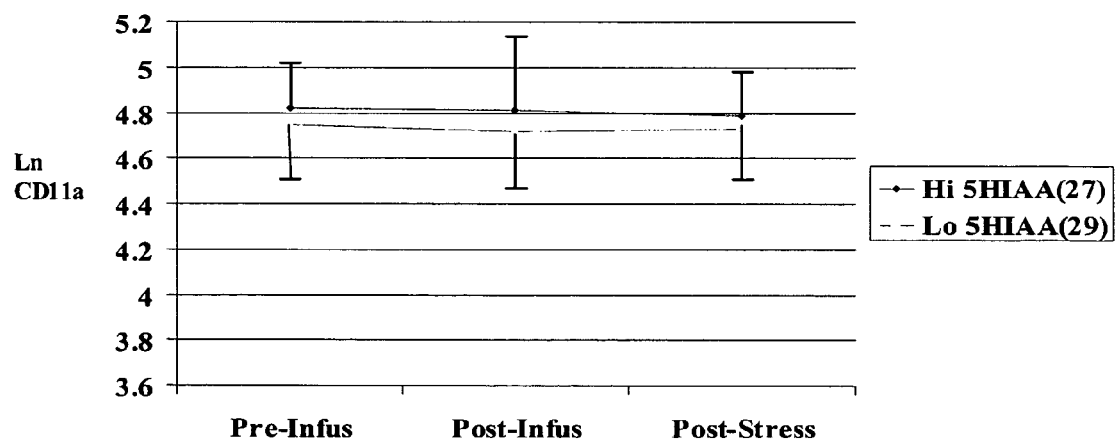

Fig. 29. CSF 5HIAA & CD-11a Response to Tryptophan Infusion & Stress
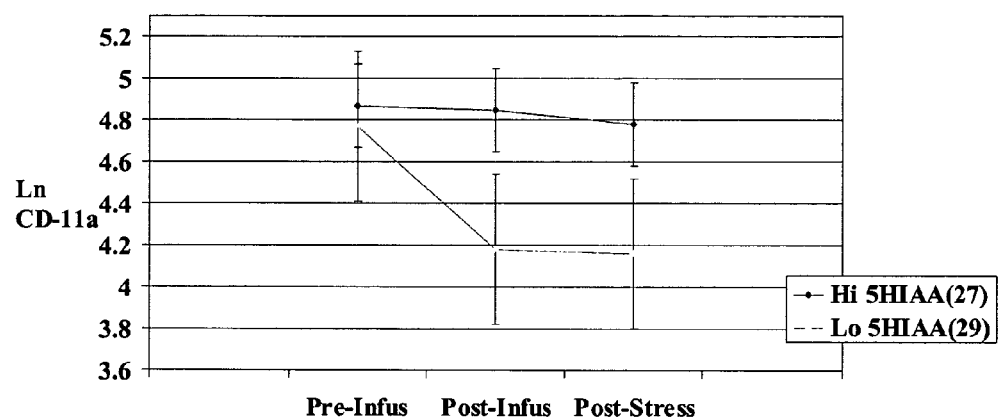
Fig. 30. CSF 5HIAA & CD-11b Response to Tryptophan Infusion & Stress
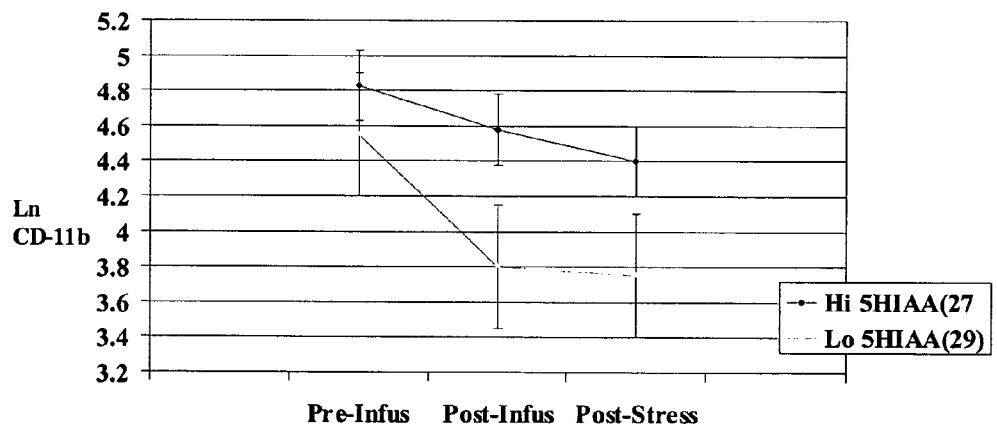

Fig. 31. CSF 5HIAA & CD-11c Response to Tryptophan Infusion & Stress
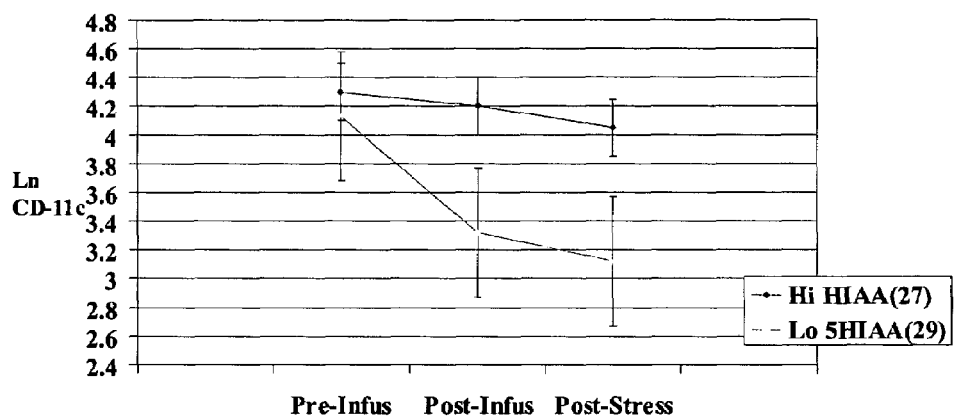
Fig. 32. CSF 5HIAA & HLA-DR Response to Tryptophan Infusion & Stress
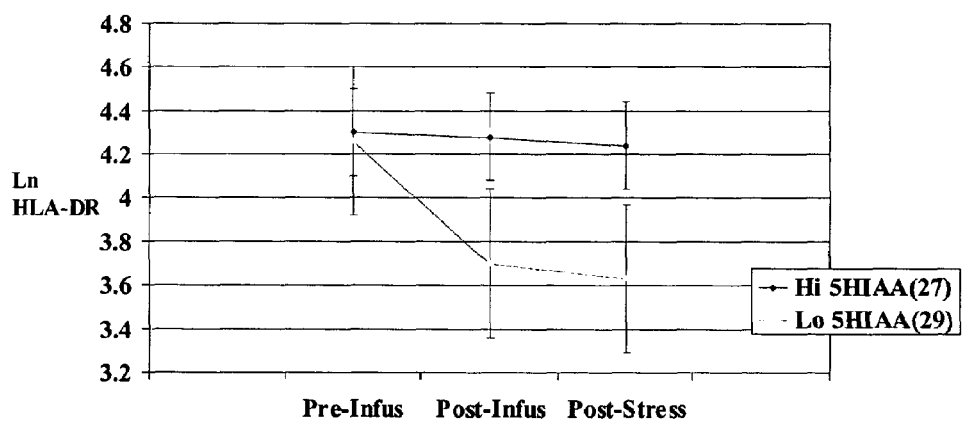

Fig. 33. 5HTTLPR Genotypes & CD-11A Response to Tryptophan Depletion & Stress
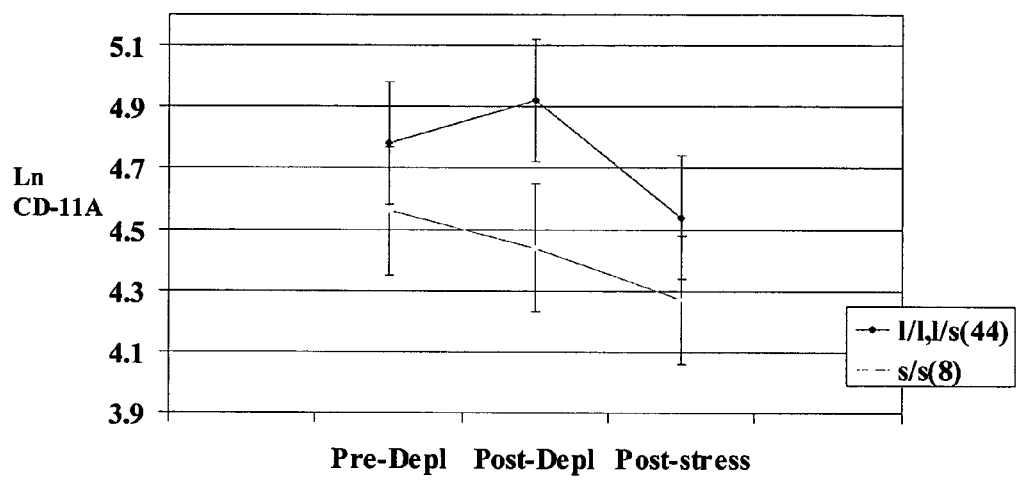
Fig. 34. 5HTTLPR Genotypes & HLA-DR Response to Tryptophan Depletion & Stress
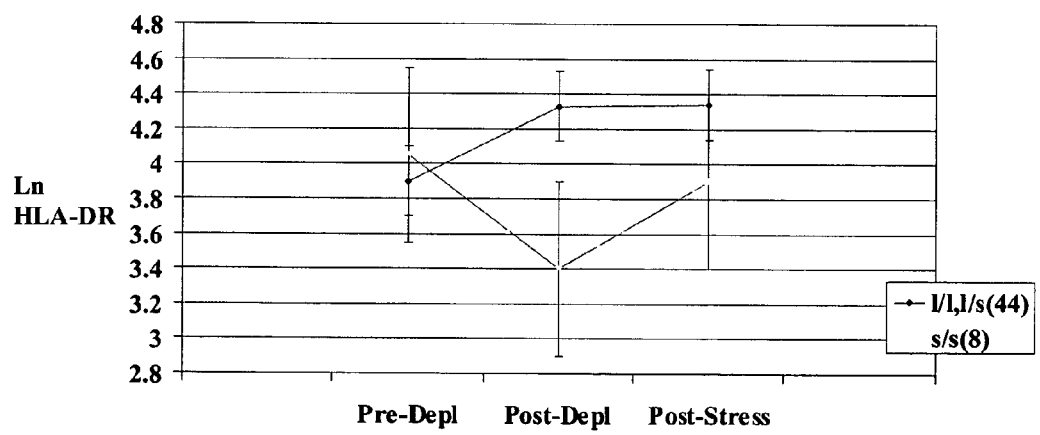

USE OF POLYMORPHISM OF THE SEROTONIN TRANSPORTER GENE PROMOTER AS A PREDICTOR OF DISEASE RISK

RELATED APPLICATIONS

This application is a continuation of U.S. patent application Ser. No. 09/698,870, filed Oct. 27, 2000 now abandoned, and claims the benefit of U.S. provisional patent application Ser. No. 60/162,390, filed Oct. 29, 1999, the disclosures of which is incorporated by reference herein in their entirety.

STATEMENT OF GOVERNMENT SUPPORT

The present invention was made with Government support under grant number PO1 HL36587 from the National Heart, Lung, and Blood Institute. The Government has certain rights to this invention.

FIELD OF THE INVENTION

The present invention concerns methods of screening subjects for risk of disease.

BACKGROUND OF THE INVENTION

It is known that stress can contribute to a variety of different physical diseases. However, it is not well understood why different individuals respond to stress in different ways. Because stress is such a significant contributory factor in disease, it would be extremely useful to have a way to identify individuals who are at high risk, or increased risk, of responding unfavorably to stress in a manner that increases their risk of disease.

SUMMARY OF THE INVENTION

The present invention is based on the recognition that by assessing genotypes (long vs. short alleles) of a polymorphism of the promoter region of the gene that encodes the serotonin transporter (5HTTLPR), one can identify persons who are more sensitive to stress and, therefore, at higher risk of developing a broad range of diseases. Thus, the present invention provides a method of screening subjects for disease risk. The method comprises determining the serotonin transporter gene promoter genotype (with respect to long and short alleles thereof) of a subject. The serotonin transporter gene promoter genotype is used to indicate whether or not the subject is at increased risk of disease. The method is particularly adapted to screening for risk of disease in response to stress, and accordingly can be used to indicate interventions that manage stress, and hence reduce disease risk, in susceptible or higher-risk individuals.

In one particular embodiment, the method comprises determining the presence of at least one (and preferably two) serotonin transporter gene promoter long alleles in a subject. The presence of at least one serotonin transporter gene promoter long allele (and particularly two long alleles) indicates the subject is at increased risk of disease, as compared to a subject with no long alleles, or a subject with only one long allele.

The foregoing and other aspects of the present invention are explained in greater detail below.

BRIEF DESCRIPTION OF THE DRAWINGS

FIG. 1 shows serotonin transporter genotypes and CSF 5HIAA levels.

FIG. 2 shows 5HTTLPR genotypes and Hamilton depression rating scale scores after fluvoxamine.

FIG. 3 shows 5HTTLPR genotypes and Hamilton depression rating scale scores after fluvoxamine plus pindolol.

FIG. 4 shows 5HTTLPR genotypes and mean arterial pressure responses to stress.

FIG. 5 shows CSF 5HIAA levels and mean arterial pressure responses to stress.

FIG. 6 shows 5HTTLPR genotypes and heart rate responses to stress.

FIG. 7 shows CSF 5HIAA levels and heart rate responses to stress.

FIG. 8 shows 5HTTLPR genotypes and epinephrine levels on sham tryptophan depletion day.

FIG. 9 shows 5HTTLPR genotypes and epinephrine levels on active tryptophan depletion day.

FIG. 10 shows 5HTTLPR genotypes and norepinephrine levels on sham tryptophan depletion day.

FIG. 11 shows 5HTTLPR genotypes and norepinephrine levels on active tryptophan depletion day.

FIG. 12 shows CSF 5HIAA levels and norepinephrine levels on sham tryptophan depletion day.

FIG. 13 shows CSF 5HIAA levels and norepinephrine levels on active tryptophan depletion day.

FIG. 14 shows CSF 5HIAA levels and norepinephrine levels on sham tryptophan infusion day.

FIG. 15 shows CSF 5HIAA levels and norepinephrine levels on active tryptophan infusion day.

FIG. 16 shows 5HTTLPR genotypes and cortisol levels on sham tryptophan depletion day.

FIG. 17 shows 5HTTLPR genotypes and cortisol levels on active tryptophan depletion day.

FIG. 18 shows CSF 5HIAA level and cortisol levels on sham tryptophan depletion day.

FIG. 19 shows CSF 5HIAA level and cortisol levels on active tryptophan depletion day.

FIG. 20 shows CSF 5HIAA level and cortisol levels on sham tryptophan infusion day.

FIG. 21 shows CSF 5HIAA level and cortisol levels on active tryptophan infusion day.

FIG. 22 shows CSF 5HIAA levels and prolactin levels on sham tryptophan infusion day.

FIG. 23 shows CSF 5HIAA levels and prolactin levels on active tryptophan infusion day.

FIG. 24 shows CSF 5HIAA levels and prolactin levels on sham tryptophan depletion day.

FIG. 25 shows CSF 5HIAA levels and prolactin levels on active tryptophan depletion day.

FIG. 26 shows 5HTTLPR genotypes and prolactin levels on sham tryptophan depletion day.

FIG. 27 shows 5HTTLPR genotypes and prolactin levels on active tryptophan depletion day.

FIG. 28 shows CSF 5HIAA and CD11a response to sham (saline) infusion and stress.

FIG. 29 shows CSF 5HIAA and CD-11a response to tryptophan infusion and stress.

FIG. 30 shows CSF 5HIAA and CD-11b response to tryptophan infusion and stress.

FIG. 31 shows CSF 5HIAA and CD-11c response to tryptophan infusion and stress.

FIG. 32 shows CSF 5HIAA and HLA-DR response to tryptophan infusion and stress.

FIG. 33 shows 5HTTLPR genotypes and CD-11a response to tryptophan depletion and stress.

FIG. 34 shows 5HTTLPR genotypes and HLA-DR response to tryptophan depletion and stress.

DETAILED DESCRIPTION OF THE INVENTION

"Disease" as used herein refers to physical disease, and not mental or psychiatric disease.

"Stress" as used herein refers to any physical or psychological stimulus that induces a physiological stress response in a subject (e.g., increased heart rate, increased blood pressure, and/or increased levels of hormones such adrenalin or cortisol). Such stress may be an acute stress or a chronic stress.

"Subjects" as referred to herein are primarily male and female human subjects, including juvenile, adolescent, and adult subjects.

The serotonin transporter is known, see, e.g., U.S. Pat. No. 5,418,162 to Blakely et al. The long and short alleles of the serotonin transporter gene promoter region (5HTTLPR) known, see, e.g., K. Lesch et al., Science 274, 157-1531 (1996), and can be detected in a subject in accordance with known techniques.

The presence of one or two long alleles of the serotonin transporter promoter region (5HTTLPR) may be detected or determined either directly or indirectly by any suitable means. A variety of techniques are known to those skilled in the art. All generally involve the step of collecting a sample of biological material containing DNA from the subject, and then detecting whether or not the subject possesses DNA corresponding to or indicative of the long or short allele. Detection is typically carried out with an oligonucleotide probe that specifically binds to one or the other allele, and subsequent amplification of the targeted probe or DNA with a procedure such as polymnerase chain reaction. Any biological sample which contains the DNA of that subject may be employed, including tissue samples and blood samples, with blood cells being a particularly convenient source. For example, DNA may be prepared from peripheral blood samples, followed by polymerase chain reaction to amplify the relevant sequence. Analysis of the polymorphism may be carried out by denaturing gel electrophoresis, in accordance with known techniques. A kit for carrying out such tests would typically include an oligonucleotide probe that selectively distinguishes the long or short alleles, instructions for carrying out the test, and optionally instructions for advising the subject on potential interventions, all of which may be packaged together in a common container.

Diseases with which the instant invention is concerned are, as noted above, physical diseases. Such diseases are those that are influenced by sympathetic, cortisol, and/or immune function in the individual. Examples of such physical diseases include, but are not limited to cardiovascular disease (e.g., high blood pressure, coronary heart disease, atrial and ventricular arrhythmias, stroke, etc.), infectious disease including opportunistic infections (e.g., diseases of viral, bacterial, protozoal, spirochetal, fungal, or other microbial origin such as the common cold, influenza, pneumonia, *Pneumocystis carinii* pneumonia, *staphylococcus* infection, Lyme disease, tuberculosis, thrush, mononucleosis, etc.), asthma, diabetes (type I and type II), obesity, cancer (e.g., lung, breast, colon, skin, ovarian, liver, kidney and prostate cancers, leukemia and lymphoma, etc.), autoimmune disease (e.g., rheumatoid arthritis, multiple sclerosis, Grave's disease, systemic lupus erythromatosis, etc.), amyotrophic lateral sclerosis, delayed wound healing, gastrointestinal disease (e.g., peptic ulcer, ulcerative colitis, irritable bowel syndrome, constipation, diarrhea, etc.), premenstrual syndrome, etc.

The ability to identify subjects at increased risk or higher risk of disease makes possible the application of interventions, both behavioral and biological, to reduce their risk and prevent the development of major, and even life threatening, illnesses, with a consequent savings of life, productivity, and medical care costs. For example, an increased risk individual may be indicated to make dietary or other lifestyle adjustments, may be indicated to be a candidate for blood pressure medication to control high blood pressure in what would otherwise be borderline high blood pressure situations, etc.

The present invention is explained in greater detail in the following non-limiting Examples. As used herein "5HIAA" refers to 5-hydroxyindolacetic acid; "CSF" means cerebrospinal fluid, and "CNS" means central nervous system.

EXAMPLE 1

Methods and Procedures

Subjects. Subjects in this ongoing study were admitted to the General Clinical Research Center (GCRC) at Duke University Medical Center for a 2.5 day protocol that involves lumbar puncture to obtain CSF followed by randomization to either CNS serotonin enhancement (using tryptophan infusion) or CNS serotonin depletion (using tryptophan depletion) arms, with sham infusion or depletion on the first test day followed by active depletion or infusion on the second test day. Since the focus of this report is on the effect of CNS serotonin function on biological responses to stress in the normal state, stress response data is reported here for the first day's testing in the sham depletion and infusion arms, when CNS serotonin function has not been manipulated.

Subjects are recruited via ads in the public media, flyers distributed in supermarkets and other public locations, and via outreach screening events at civic organizations and other public events, e.g., street fairs. The findings reported here are based on data obtained from the 54 subjects studied to date (age range 18-49, 56% white, 67% male).

Procedures. After being screened to exclude those with medical or psychiatric disorders or current medication use and giving informed consent, subjects reported to the GCRC during the early afternoon. After completing admission procedures, they undergo lumbar puncture, performed by a board-certified anesthesiologist. Initially, as in published studies (Roy A, Adinoff B, & Linnoila M. Acting out hostility in normal volunteers: Negative correlation with levels of 5-HIAA in cerebrospinal fluid. Psychiatry Res 1988; 24:187-94) 10-12 cc of CSF was obtained, which was mixed (to abolish the expected gradient across successive samples during the collection) and then separated into 2-cc aliquots and frozen for later assay of monoamine metabolites using HPLC. The not unexpected 10-15% incidence of post-tap headaches among the first female subjects led to the determination of whether there is a gradient of 5HIAA levels in the next two subjects. There was no gradient, with 5HIAA concentrations in cc 11-12 being virtually identical to those in cc 1-2. A previous study (Nordin C, Lindstrom L, Wieselgren I M. Acid monoamine metabolites in the CSF of healthy controls punctured without preceding strict bedrest: A retrospective study. J Psychiatr Res 1996; 30: 127-33) found that without strict bedrest prior to the lumbar puncture, body height was unrelated to CSF 5HIAA levels. Since the subjects had been ambulatory prior to lumbar puncture, it appears, therefore, that CSF in the lumbar column had been mixed by their movements, thereby abolishing any gradient due to height. This has allowed the use of a smaller needle to obtain only 3-4 cc of CSF, thereby greatly reducing the incidence of post-tap headaches Between 11 AM and noon on the first test day, following the sham depletion or infusion, all subjects underwent a 45-minute mental stress protocol during which cardiovascular function was monitored. This began with a 5-minute rest period, followed by 5 minutes of reading from a neutral text, followed by a 5-minute anger recall task, a second 5-minute neutral reading task, and a 5-minute sadness recall task. Additional 5-minute rest periods followed each 5-minute stress period.

Measures. Blood pressure and heart rate were determined at one-minute intervals using a Critikon (Tampa, Fla., USA) automatic vital signs monitor. To determine 5HTTLPR genotypes, genomic DNA was extracted by standard procedure (Puregene D-50K Isolation Kit, Gentra, Minneapolis, Minn.) from fresh or frozen samples of peripheral blood collected from the subjects. Polymerase chain reaction amplification to generate a 484- or 528-base pair fragment corresponding to the short (s) and long (l) 5HTTLPR alleles, respectively, was carried out as described elsewhere (Lesch K P, Bengel D, Heils A, Sabol S Z, Greenberg B, Petri S, Benjamin J, Muller C R, Hamer D H, Murphy D L. Association of anxiety-related traits with a polymorphism in the serotonin transporter gene regulatory region. Science 1996; 274:1527-31) with the following modifications: 100 ng of genomic DNA was used in each reaction mixture, dGTP was substituted for 7-deaza-2'-dGTP, and the final volume of each reaction mixture was 25 microliters. The fragments were resolved by electrophoresis through 3% agarose gels. 5-Hydroxyindoleacetic acid, the primary serotonin metabolite (5HIAA) was measured by high-pressure liquid chromatography with electrochemical detection. The method used is a trace-enrichment method that utilized sequential C-18 columns for samples cleanup and analytical separation (Higley J D, Linnoila M. Low central nervous system serotonergic activity is traitlike and correlates with impulsive behavior. A nonhuman primate model investigating genetic and environmental influences on neurotransmission. Ann NY Acad Sci 1997; 29:39-56). Samples were diluted in 0.2 N PCA containing 0.5 mM EDTA and 0.5 mM sodium metabisulfite, and injected directly onto the HPLC. The sample is enriched on a C18 precolumn using an aqueous mobile phase composed of 0.05 M citrate, 0.05 M dibasic sodium phosphate, 0.5 mM EDTA at pH 3.5. Then the sample is eluted onto a Waters Spherisorb 3 uM ODS2 C18 column with a mobile phase containing 4-8% acetonitrile in addition to the components of the enrichment mobile phase. Samples are detected by electrochemical detection, with a detector potential set at +0.55 mV vs. Ag/AgCl reference electrode. Data are collected with a computer-based data collection system, and quantitated with the use of internal standard and external standard curves. Sensitivity of the assay is 0.5 ng/samp Statistical Analysis. One-way ANOVA was used to compare CSF 5HIAA levels in 5HTTLPR genotype groups, and two-way repeated measures ANOVA was used to evaluate changes in cardiovascular measures between rest and stress periods as a function of CSF 5HIAA (high vs. low, based on median split) or 5HTTLPR (l/l, l/s, s/s genotypes) groups. Sample sizes vary across analyses due to loss of data in subjects who experienced post-tap headache or were unable to complete ingestion of the amino acid capsules required for sham tryptophan depletion.

EXAMPLE 2

Central Nervous System Serotonin Function and Cardiovascular Responses to Stress As shown in FIG. 1, subjects with one or two copies of the more functional long (l) allele of the 5HTTLPR have CSF 5HIAA levels that are 50% higher than shown in subjects with the s/s allelotype, with the 5HTTLPR genotype accounting for 13% of the variance in CSF 5HIAA. Although applicants do not wish to be bound to any particular theory of the invention, This is probably the result of persons with one or more copies of the l allele having more transporter sites on presynaptic nerves. This results in more rapid clearance of previously released 5HT from the extraneuronal space, which, in turn, means less stimulation of inhibitory $5HT_{1A}$ somatodendritic autoreceptors. A higher level of 5HT release results, thereby accounting for the higher CSF 5HIAA levels in persons with the l allele. Supporting this interpretation are results from a clinical study by Smeraldi et al., *Molecular Psychiatry* 3, 508-11 (1998). As shown in FIG. 2, depressed patients with the s/s allelotype show a slower clinical improvement following start of SSRI treatment than patients with one or two l alleles, consistent with slower clearance of 5HT (due to fewer transporter sites) in the s/s patients producing more pronounced inhibition of 5HT release due to increased stimulation of inhibitory autoreceptors. Strongly supporting this mechanism, when s/s patients are treated with the $5HT_{1A}$ antagonist pindolol, they show (FIG. 3) as rapid a clinical improvement as patients with the l alllele.

Both 5HTTLPR allelotype—dichotomized as l/l and l/s vs. s/s, since l/l and l/s have similar CSF 5HIAA levels and are both 50% higher than s/s (FIG. 1)—and CSF 5HIAA levels (high vs. low, median split) are associated with differential cardiovascular responsivity to mental stress. As shown in FIGS. 4 and 5, MAP at rest does not differ as a function of either 5HTTLPR allelotype or 5HIAA level, but subjects with at least one l allele or high 5HIAA show robustly larger MAP rises during the stress periods. A similar pattern is seen (FIGS. 6 and 7) in HR at rest and during stress.

These findings indicate that CNS 5HT function is regulated by the l allele of the 5HTTLPR in an autosomal dominant fashion, with persons having one or two copies of the l allele having increased levels of 5HT release, as indexed by CSF 5HIAA levels. Moreover, persons with either the l allele or higher 5HIAA levels exhibit significantly larger MAP and HR responses to stress than their s/s or low 5HIAA counterparts. These findings indicate that the l allele is a marker—via repeated larger pressor responses—for increased risk of cardiovascular disease under conditions of chronic stress. This cardiovascular correlate of the l allele could account for the marked global population variation in frequency of the l allele—from 70%+ in Africa (and African Americans) to 50-60% in Europe to <30% in China and Japan. The cardiovascular hyperreactivity in persons with the l allele could have conferred some selection advantage under persisting conditions in Africa, but without migration to colder or more populous/socially complex conditions, this advantage could have disappeared or even become a disadvantage. The increased frequency of the l allele could be responsible, in part, for the increased incidence of hypertension among African Americans. It can also serve as a marker for stress-related cardiovascular disease. As shown below, the neuroendocrine and immune system correlates of 5HTTLPR allelotypes indicate a role for this polymorphism in a wide range of medical disorders.

EXAMPLE 3

CNS Serotonin Function and Catecholamine Response to Stress

An amino acid drink either containing or lacking tryptophan is used to effect either sham tryptophan depletion or active tryptophan depletion. As shown in FIG. 8, with sham tryptophan depletion (amino acid drink contains tryptophan), the pre-drink and post-drink stress levels of plasma epinephrine are identical between subjects with one or two l alleles and those with the s/s allelotype. In marked contrast, with active depletion (drink free of tryptophan), though not different prior to the drink, subjects with the l allele show higher epinephrine levels after the drink and those with the s/s allelotype show lower levels—a very robust effect, as can be appreciated from the nonoverlapping SEMs.

This pattern of responses is consistent with their increased CNS 5HT release (FIG. 1) causing a down regulation of the 5HT receptors (probably in the hypothalamus) that are known to inhibit SNS outflow among persons with one or two l alleles. With no manipulation of CNS 5HT release (sham depletion day), this down regulation leads them to have identical SNS outflow, as indexed by epinephrine levels, as subjects with the s/s allelotype. In contrast, with decreased CNS 5HT release (active depletion day), withdrawal of 5HT leads to a larger SNS disinhibition in l allele subjects, while subjects with the s/s allelotype (and upregulated 5HT receptors mediating SNS inhibition) show a reduction in epinephrine levels following depletion. A similar, but less pronounced, pattern (not shown) was seen with high 5HIAA subjects showing only a tendency toward higher epinephrine levels following depletion.

The pattern of norepinephrine response with sham and active depletion is more complex than that just described for epinephrine, as illustrated by FIGS. 10-13. As indicated, there does appear to be a tendency for those with l alleles or high 5HIAA to have higher SNS outflow as indexed by norepinephrine levels.

Norepinephrine responses to sham and active enhancement of CNS 5HT release, via tryptophan infusion, were evaluated. As shown in FIG. 14, on the sham infusion day, both high and low 5HIAA subjects showed a similar increase in plasma norepinephrine levels. In contrast, with active tryptophan infusion, FIG. 15, there was a similar decrease in norepinephrine levels, presumably the result of stimulation of the aforementioned hypothalamic 5HT receptors that inhibit SNS outflow. It will be important as more subjects with the s/s allelotype are run in the tryptophan infusion arm, to see if those with the l allele show a greater inhibition to tryptophan infusion. In comparison, the 5HTTLPR allelotypes showed highly significant differential epinephrine response to tryptophan depletion (FIG. 9), with the effect due to 5HIAA levels being much weaker. These finding suggest that the 5HTTLPR effect on SNS outflow is via additional, or other pathways than is indicated by CSF 5HIAA.

EXAMPLE 4

CNS Serotonin Function and Cortisol Response to Stress

As shown in FIGS. 16-19, there is a tendency for subjects with the l allele or high 5HIAA to start at 7 AM ("Pre") with similar cortisols and then to have higher levels of cortisol during the stress protocol after consuming the amino acid drink on the sham depletion day. In contrast, subjects with a s/s allelotype and high 5HIAA subjects exhibit higher cortisol levels during the stress protocol after active tryptophan depletion.

With regard to tryptophan infusion, as shown in FIG. 20, on the sham (saline) infusion day, subjects with high and low CSF 5HIAA show an identical pattern of cortisol levels, starting higher at the 7 AM Pre blood draw, falling at the time of the initial baseline draw at 11 AM, and then showing a rise across the stress protocol. In marked contrast, with infusion of tryptophan (FIG. 21), there was less of a fall at the initial baseline (which occurred 45 min. after the tryptophan infusion), followed by a gradual divergence of cortisol levels, with low 5HIAA subjects maintaining high levels and high 5HIAA subjects showing a marked decline in cortisol toward the end of the stress protocol. This pattern of response is consistent with low 5HIAA subjects having upregulation of the 5HT receptors that mediate HPA axis activation, accounting for their maintaining higher cortisol levels when CNS 5HT release was enhanced by tryptophan infusion.

EXAMPLE 5

CNS Serotonin Function and Prolactin Response to Stress

As shown in FIG. 22, on the sham infusion day, there was the expected fall in plasma prolactin from the 7 AM Pre level to the initial baseline at 11 AM, 45 min. after the sham (saline) infusion, with a gradual rise during the ensuing stress protocol. On the active tryptophan infusion day, FIG. 23, there was less of a fall due to the prolactin rise to tryptophan infusion during the 45 min. following the infusion (not shown), with a continuing gradual fall from those high levels across the stress protocol.

The pattern of prolactin response on both sham and active days of the depletion arm was dramatically different. As shown in FIGS. 24-27, both low 5HIAA and s/s allelotype subjects showed the same fall in prolactin levels following the amino acid drink on both sham and active depletion days. In marked contrast, both high 5HIAA and l allelotype subjects maintained high prolactin levels from the 7 AM Pre level across the stress protocol commencing at 11 AM after drinking either the amino acid drink with (sham day) or without (active depletion day) tryptophan depletion. The only difference between the subjects' experience on the saline infusion day (FIG. 22) vs. the sham or active depletion day (FIGS. 24-26) was the nausea experienced by nearly all subjects after drinking the amino acid drink with or without tryptophan. Since nausea involves $5HT_3$ receptors in the brain stem, it appears likely that activation of these receptors somehow prevented the prolactin fall, but only in subjects with high 5HIAA levels or the l allele.

EXAMPLE 6

CNS Serotonin Function and Immune Function in Response to Stress

As shown in FIG. 28, subjects with high and low CSF 5HIAA levels showed similar levels of CD11a (an adhesion molecule) expression on monocytes before and after sham depletion and after the stress protocol. There was a similar lack of difference in expression of any of the other adhesion molecules or cytokines as a function of either 5HTTLPR allelotype or CSF 5HIAA on both sham depletion and sham infusion days. In marked contrast, as shown in FIGS. 29-32, after active tryptophan depletion, subjects with low 5HIAA levels show a decrease in expression of adhesion molecules CD11a, CD11b, and CD11c and HLA-DR (MHC-III, which monocytes use to present processed antigens to other immune system cells).

As show in FIGS. 33-35, there is a differential response of CD11A, HLA-DR, and TNF-alpha expression to tryptophan depletion as a function of 5HTTLPR. Again, with sham depletion there were no differences in expression of these markers, but following active tryptophan depletion, subjects with the s/s allelotype showed decreases in these markers while subjects with l/l or l/s allelotypes showed increases.

A remarkably broad range of biological responses that appear to be affected by CNS 5HT function as indexed by the 5HTTLPR polymorphism or its correlate CSF 5HIAA, including the cardiovascular, neuroendocrine, and immune systems. Some of these effects are clearly quite large, given the robust statistical significance levels and clear differences that are evident even from inspection of curves with SEMs not overlapping.

The foregoing is illustrative of the present invention, and is not to be construed as limiting thereof. The invention is defined by the following claims, with equivalents of the claims to be included therein.

The invention claimed is:

1. A method of identifying a human subject having an increased likelihood of having larger mean arterial pressure rises in response to psychological stress, comprising detecting the presence of at least one serotonin transporter gene promoter long allele in the human subject, wherein the detection of at least one serotonin transporter gene promoter long allele in the human subject identifies the human subject as having an increased likelihood of having larger mean arterial pressure rises in response to psychological stress, as compared to human subjects homozygous for the short allele.

2. A method of identifying a human subject having an increased likelihood of developing a cardiovascular disease in response to having larger mean arterial pressure rises in response to psychological stress, comprising detecting the presence of at least one serotonin transporter gene promoter long allele in the human subject, wherein the detection of at least one serotonin transporter gene promoter long allele in the human subject identifies the human subject as having an increased likelihood of having larger mean arterial pressure rises in response to psychological stress and thereby as having an increased likelihood of developing a cardiovascular disease in response to having larger mean arterial pressure rises in response to psychological stress, as compared to human subjects homozygous for the short allele.

3. The method of claim 2, wherein the cardiovascular disease is hypertension.

4. The method of claim 2, wherein the cardiovascular disease is coronary heart disease.

5. The method of claim 2, wherein the cardiovascular disease is stroke.

* * * * *